United States Patent
Hada et al.

(10) Patent No.: US 8,721,856 B2
(45) Date of Patent: May 13, 2014

(54) GAS SENSOR CONTROL SYSTEM ENSURING INCREASED MEASUREMENT ACCURACY

(75) Inventors: Satoshi Hada, Inazawa (JP); Takayuki Ishikawa, Anjo (JP); Katsuhide Akimoto, Nishio (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 665 days.

(21) Appl. No.: 12/407,970

(22) Filed: Mar. 20, 2009

(65) Prior Publication Data

US 2009/0236223 A1 Sep. 24, 2009

(30) Foreign Application Priority Data

Mar. 20, 2008 (JP) ................ 2008-072626

(51) Int. Cl.
*G01N 27/407* (2006.01)
*G01N 27/406* (2006.01)
*G01N 27/409* (2006.01)

(52) U.S. Cl.
CPC .......... *G01N 27/406* (2013.01); *G01N 27/4062* (2013.01); *G01N 27/409* (2013.01); *G01N 27/407* (2013.01)
USPC ........... 204/424; 204/425; 204/426; 204/427; 204/428; 204/429; 73/23.31; 73/23.32

(58) Field of Classification Search
CPC .. G01N 27/406; G01N 27/407; G01N 27/409
USPC ............... 204/406, 421–429; 205/781, 784.5, 205/788; 73/23.31–23.32
See application file for complete search history.

(56) References Cited

U.S. PATENT DOCUMENTS

| | | | | |
|---|---|---|---|---|
| 5,034,112 A * | 7/1991 | Murase et al. | ................ | 204/406 |
| 5,100,530 A * | 3/1992 | Dorr et al. | ................ | 204/406 |
| 5,558,752 A * | 9/1996 | Wang et al. | ................ | 204/401 |
| 5,810,997 A | 9/1998 | Okazaki et al. | | |
| 7,180,596 B2 * | 2/2007 | Haraguchi et al. | ............ | 356/437 |
| 2002/0011410 A1* | 1/2002 | Inoue et al. | ................ | 204/426 |
| 2004/0045824 A1* | 3/2004 | Hada et al. | ................ | 204/425 |
| 2004/0050695 A1* | 3/2004 | Haraguchi et al. | ............ | 204/424 |
| 2004/0089545 A1 | 5/2004 | Kawase et al. | | |
| 2005/0230248 A1 | 10/2005 | Kawase et al. | | |
| 2007/0272551 A1* | 11/2007 | Inagaki et al. | ................ | 204/406 |

FOREIGN PATENT DOCUMENTS

| | | |
|---|---|---|
| JP | H09-061397 | 3/1997 |
| JP | 2004-108788 | 4/2004 |
| JP | 2004-205488 | 7/2004 |
| JP | 2005-326388 | 11/2005 |
| JP | 2006-071429 | 3/2006 |

* cited by examiner

*Primary Examiner* — Bach Dinh
(74) *Attorney, Agent, or Firm* — Nixon & Vanderhye PC (57) ABSTRACT

A gas sensor control system for a gas sensor having a first, a second, and a third cell. The second cell produces a second cell electric current indicating the concentration of oxygen in gas in which the amount of oxygen has already been controlled by the first cell. The third cell produces a third cell electric current indicating the concentration of a preselected component of the gas in which the amount of oxygen has already been controlled by the first cell. A second cell circuit converts the second cell electric current into a voltage as a second cell current-measured value. A current adjuster produces a flow of an adjustment current as a function of the second cell current-measured value so that a third cell circuit converts the third cell electric current minus the adjustment current into a voltage as representing the concentration of the preselected component of the gas.

2 Claims, 6 Drawing Sheets

GAS SENSOR CONTROL SYSTEM ENSURING INCREASED MEASUREMENT ACCURACY

CROSS REFERENCE TO RELATED DOCUMENT

The present application claims the benefit of Japanese Patent Application No. 2008-72626 filed on Mar. 20, 2008, the disclosures of which are incorporated herein by reference.

BACKGROUND OF THE INVENTION

1. Technical Field of the Invention

The present invention relates generally to a gas sensor control system which is designed to sample an output from a gas sensor such as a NOx sensor to determine the concentration of gas, as measured by the gas sensor, accurately.

2. Background Art

Recently, automotive emission regulations and fuel efficiency requirements have been more tightened. For instance, there are increasing needs for techniques for reducing the amount of NOx emissions from diesel engines or diagnosing a NOx purifier. Modern gasoline engines are controlled to burn fuel over a fuel-lean range in order to improve the fuel efficiency, thus resulting in an increase in amount of NOx emissions. Techniques for controlling the NOx emissions or diagnosing the NOx purifier are, therefore, been required. For these reasons, NOx sensors are increasingly demanded.

The NOx sensors are typically of a multi-cell structure using a zirconia made solid electrolyte body. For example, the NOx sensors are equipped with a pump cell, a monitor cell, and a sensor cell which are made of solid electrolyte. The pump cell works to keep the concentration of oxygen ($O_2$), as contained in exhaust gas introduced into a gas chamber of the NOx sensor, at a constant value. The monitor cell works to measure the concentration of NOx contained in the exhaust gas from which the oxygen has been removed by the pump cell. Similarly, the sensor cell works to measure the concentration of NOx contained in the exhaust gas from which the oxygen has been removed by the pump cell.

Japanese Patent First Publication No. 2004-108788 teaches a gas sensor control system using the above type of NOx sensor. The gas sensor control system is designed to measure an electric current flowing through the sensor cell (which will also be referred to below as a sensor cell current Is) and an electric current flowing through the monitor cell (which will also be referred to below as a monitor cell current Im) using measuring circuits, calculate a difference between the sensor cell current Is and the monitor cell current Im (i.e., Is−Im), and determine the concentration of NOx as a function of such a difference. This enables the concentration of NOx to be determined regardless of the concentration of oxygen contained in gas introduced into the gas chamber of the NOx sensor.

The sensor cell current Is, as produced by the sensor cell of the above type of NOx sensor, usually includes a current component arising from to the concentration of NOx to be measured and a current component arising from the concentration of oxygen remaining in the gas chamber of the NOx sensor, thus causing the resolution of the measuring circuit in measuring the sensor cell current Is to be decreased by an amount corresponding to the concentration of oxygen remaining in the gas chamber. The sensor cell current Is that is a function of the concentration of NOx is very faint in level of the order of nA, which results in an increase in ratio of the current component arising from the concentration of oxygen to that arising from the concentration of NOx. There is left a room for improvement of accuracy in measuring the concentration of NOx.

SUMMARY OF THE INVENTION

It is therefore a principal object of the present invention to avoid the disadvantages of the prior art.

It is another object of the present invention to provide a gas sensor control system designed to ensure increased accuracy in measuring the concentration of a gas component such as NOx.

According to one aspect of the invention, there is provided a gas sensor control system designed to control an operation of a gas sensor, such as a NOx sensor, equipped with a sensing device including a first cell, a second cell, and a third cell which are each made of a solid electrolyte and a gas chamber formed therein. The first cell works to control the amount of oxygen contained in a gas admitted into the gas chamber to keep the concentration of oxygen in the gas at a given controlled level. The second cell works to produce an electric current as a function of the concentration of oxygen contained in the gas in which the amount of oxygen has already been controlled by the first cell. The third cell works to produce an electric current as a function of the concentration of a preselected component of the gas in which the amount of oxygen has already been controlled by the first cell. The gas sensor control system comprises: (a) a second cell circuit including a current-to-voltage converter which is connected to the second cell to sample and convert the electric current, as produced by the second cell, into a voltage and outputs the voltage as a second cell current-measured value; (b) a third cell circuit including a current-to-voltage converter which is connected to the third cell; (c) a current adjuster working to produce an adjustment current that is an electric current determined as a function of the second cell current-measured value, as outputted from the second cell circuit; and (d) a branch circuit path which is connected to a junction between the current-to-voltage converter of the third cell circuit and the third cell and through which the adjustment current flows to input the electric current, as produced by the third cell, minus the adjustment current into the current-to-voltage converter of the third cell circuit, so that the current-to-voltage converter converts the electric current minus the adjustment current into a voltage and outputs the voltage as a third cell current-measured value representing the concentration of the preselected component of the gas.

Specifically, in the above type of gas sensors, a current component, as developed by decomposition of oxygen remaining in the gas chamber, and a current component, as developed by decomposition of the preselected component of the gas, flow through the third cell. The electric current, as produced by the third cell, thus contains a combination of the two current components undesirably.

In order to alleviate the above problem, the current adjuster works to produce the adjustment current as a function of the second cell current-measured value, as outputted from the second cell circuit, and input it to the current-to-voltage converter of the third cell circuit together with the electric current, as produced by the third cell, so that the electric current, as produced by the third cell, minus the adjustment current enters the current-to-voltage converter of the third cell circuit. The current-to-voltage converter, therefore, converts the electric current minus the adjustment current into the voltage and outputs it as the third cell current-measured value representing the concentration of the preselected component of the gas. Specifically, the current smaller in level than that produced by the third cell flows into the current-to-voltage converter, thereby resulting in an increased resolution in the current-to-voltage conversion in the third cell circuit, which leads to an improved accuracy in measuring the concentration of the preselected component of the gas.

In the preferred mode of the invention, the current adjuster is connected to an output terminal of the second cell circuit and works to determine the adjustment current based on the second cell current-measured value, as outputted from the second cell circuit and establish a flow of the adjustment current through the branch circuit path in a direction in which the adjustment current is drawn from the third cell circuit.

The current adjuster may produce the adjustment current which is identical with the electric current, as produced by the second cell.

The current adjuster is designed to regulate a difference between a sensitivity of the second cell to produce the electric current in response to the concentration of oxygen and that of the third cell to produce the electric current in response to the concentration of oxygen.

The current adjuster may be equipped with a differential amplifier which has one of two input terminals into which the second cell current-measured value is inputted and the other input terminal to which a reference voltage is inputted and also has an output terminal connected to the branch circuit path.

The gas sensor control system may further comprise an analog-to-digital converter into which the third cell current-measured value, as outputted from the third cell circuit, is inputted and converts the third cell current-measured value into a digital signal as indicating the concentration of the preselected component of the gas.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
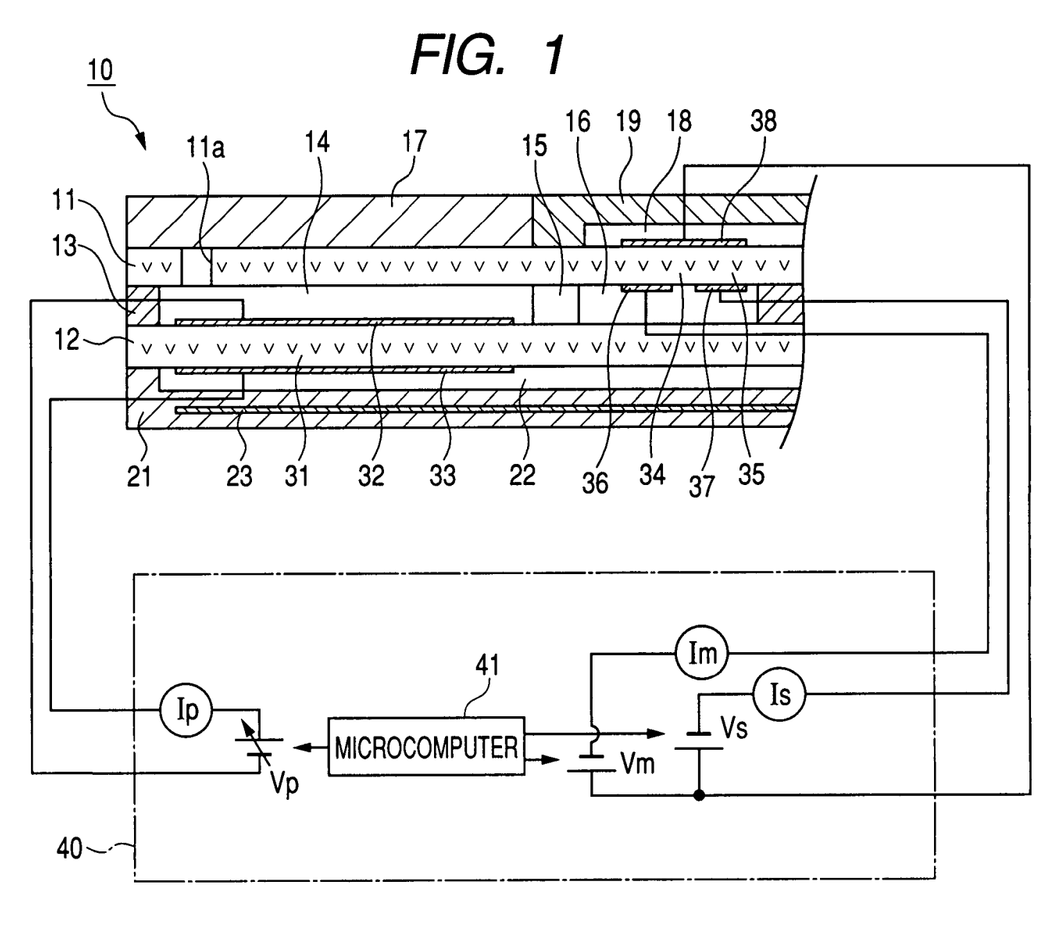
FIG. 1 is a schematic illustration which shows a gas sensor control system according to the invention and a NOx gas sensor.

Referring now to the drawings, wherein like numbers refer to like parts in several views, particularly to FIG. 1, there is shown a gas sensor control system according to the invention which is designed as a NOx concentration measuring system to sample an output of a NOx sensor installed in an exhaust pipe of an automotive internal combustion engine to determine the concentration of NOx (nitrogen oxide) contained in exhaust emissions of the engine. The engine, as referred to herein, is a diesel engine. The NOx concentration measuring system works to sample the output from the NOx sensor installed in the exhaust pipe to diagnose an operation of a NOx control catalyst such as a NOx absorber catalyst or ammonia selective catalytic reduction (SCR). For instance, the NOx sensor is disposed downstream of the NOx control catalyst. The output of the NOx sensor that is a function of the concentration of NOx contained in exhaust gas having passed through the NOx control catalyst represents the ability or degree of deterioration of the NOx control catalyst. The NOx concentration measuring system monitors the output of the NOx sensor and determines that the NOx control catalyst is malfunctioning when the monitored output is greater than a given reference value.

The NOx sensor is equipped with a sensing device 10, as illustrated in FIG. 1, which is of a laminated type (also called a planar sensor element). The sensing device 10 has a length extending laterally of the drawing. The right side portion of the sensing device 10 will also be referred to herein as a base portion which is to be secured to the exhaust pipe of the engine through a housing of the NOx sensor. The left side portion of the sensing device 10 will also be referred to as a top portion which is to be exposed to the exhaust gas of the engine. The sensing device 10 is of a three-cell structure which includes a pump cell, a sensor cell, and a monitor cell. The monitor cell, like the pump cell, works to pump oxygen molecules contained in the exhaust gas out of it and is sometimes called a sub-pump cell or second pump cell.

The sensing device 10 includes solid electrolyte layers 11 and 12 made of an oxygen ion-conductive material such as zirconia and a spacer 13 made of an insulating material such as alumina. The solid electrolyte layers 11 and 12 are laid to overlap each other through a given gap defined by the spacer 13 to form a first chamber 14 and a second chamber 16. The solid electrolyte layer 11 has formed therein a gas inlet 11a through which the exhaust gas existing around the sensing device 10 is admitted into the first chamber 14. The first chamber 14 communicates with the second chamber 16 through an orifice 15. A porous diffusion layer 17 is affixed to the solid electrolyte layer 11 to produce a given degree of resistance to which the exhaust gas is subjected while passing through the diffusion layer 17. An insulating layer 19 is also affixed to the solid electrolyte layer 11 to define an air duct 18 exposed outside the sensing device 10.

An insulating layer 21 made of alumina is affixed to the lower surface of the solid electrolyte layer 12. The insulating layer 21 has formed therein a chamber which defines an air duct 22 between itself and the lower surface of the solid electrolyte layer 12. A heater 23 is embedded in the insulating layer 21 to heat the whole of the sensing device 10 to ensure the activation of the sensing device 10. Specifically, the heater 23 is supplied with electric power from a storage battery (not shown) installed in the vehicle and works to elevate the temperature of the pump cell 31, the monitor cell 34, and the sensor cell 35 up to a controlled level to accelerate and ensure the activation thereof.

The solid electrolyte layer 12 has formed therein the pump cell 31 which faces the first chamber 14 and works to pump oxygen molecules outside or into the first chamber 14 to keep the concentration of oxygen ($O_2$) at a controlled level within the first chamber 14. The pump cell 31 is equipped with an upper and a lower electrode 32 and 33 affixed to opposed areas of the surfaces of the solid electrolyte layer 12. The upper electrode 32 is exposed to the first chamber 14 and made of material which is inactive with respect to NOx, that is, hardly decomposes NOx. When the voltage is applied to the electrodes 32 and 33, the pump cell 31 dissociates or ionizes oxygen molecules within the first chamber 14 and discharges them to the air duct 22 through the electrode 33.

The solid electrolyte layer 11 has formed therein the monitor cell 34 and the sensor cell 35 which face the second chamber 16. The monitor cell 34 works to pump the oxygen molecules out of the second chamber 16. Specifically, the monitor cell 34 ionizes the oxygen molecules remaining in the exhaust gas from which the oxygen molecules have already been pumped by the pump cell 31 out of the first chamber 14 and discharges them to the air duct 18. For instance, the monitor cell 34 may be designed to produce an electromotive force as a function of the concentration of oxygen remaining in the second chamber 16 or generate an electric current as a function of the concentration of oxygen in the second chamber 16 upon application of voltage thereto. The sensor cell 35 is designed to produce an electric current as a function of the concentration of NOx contained in the exhaust gas within the second chamber 16.

The monitor cell 34 and the sensor cell 35 are located close to each other. The monitor cell 34 has an electrode 36 exposed to the second chamber 16. Similarly, the sensor cell 35 has an electrode 37 exposed to the second chamber 16. The monitor cell 34 and the sensor cell 35 have a common electrode 38 exposed to the air duct 18. Specifically, the monitor cell 34 is formed by the electrodes 36 and 38 and a portion of the solid electrolyte layer 11 through which the electrodes 36 and 38 are opposed to each other. The sensor cell 35 is formed by the electrodes 37 and 38 and a portion of the solid electrolyte layer 11 through which the electrodes 37 and 38 are opposed to each other. The electrode 36 of the monitor cell 34 is made of noble metal such as Au—Pt that is inactive with respect to NOx. The electrode 37 of the sensor cell 35 is made of noble metal such as Pt (platinum) or Rh (rhodium) that is active with respect to NOx. For the sake of convenience, the monitor cell 34 and the sensor cell 35 are illustrated as being aligned with a flow of the exhaust gas (i.e., a lateral direction in the drawing), but are practically disposed adjacent each other in a direction perpendicular to the flow of the exhaust gas. In other words, the monitor cell 34 and the sensor cell 35 are located at the same distance from the pump cell 31 in the direction in which the exhaust gas flows.

The pump cell 31 is aligned with the monitor cell 34 and the sensor cell 35 in the lengthwise direction of the sensing device 10. The pump cell 31 is closer to the top of the sensing device 10. The monitor cell 34 and the sensor cell 35 are closer to the base of the sensing device 10 at which the NOx sensor is secured to the exhaust pipe of the engine.

The exhaust gas of the engine flowing outside the NOx sensor enters the first chamber 14 through the porous diffusion layer 17 and the gas inlet 11$a$ (i.e., a pinhole). Application of voltage Vp to the pump cell 31 through the electrodes 32 and 33 causes oxygen molecules contained in the exhaust gas to undergo dissociation or ionization, so that the oxygen ($O_2$) is pumped out of the first chamber 14 to the air duct 22. If the concentration of the oxygen ($O_2$) is lower than a desired level in the first chamber 14, a reverse voltage is applied to the pump cell 31 to pump oxygen molecules into the first chamber 14 from the air duct 22 so as to keep the concentration of oxygen ($O_2$) within the first chamber 14 at the desired level. Since the electrode 32 exposed to the first chamber 14, as described above, hardly decomposes NOx, NOx gas stays within the first chamber 14. Specifically, the pump cell 3 works to keep the concentration of oxygen ($O_2$) at a controlled lower level within the first chamber 14.

The exhaust gas, as having passed through the pump cell 31, then flows into the second chamber 16. The monitor cell 34 produces an output as a function of the concentration of oxygen ($O_2$) remaining in the exhaust gas. Specifically, voltage Vm is applied to the monitor cell 34 through the electrodes 36 and 38. The monitor cell 34 then produces an output in the form of a monitor cell current Im. Voltage Vs is applied to the sensor cell 35 through the electrodes 37 and 38. The sensor cell 35 then decomposes and reduces NOx gas to produce oxygen elements which are, in turn, discharged to the air duct 18 through the electrode 38, thereby generating an output in the form of a sensor cell current Is that is a function of the concentration of NOx contained in the exhaust gas.

The NOx concentration measuring system also includes a NOx sensor circuit 40 serving as a NOx sensor controller which is equipped with a microcomputer 41 and a control circuit, as will be described later with reference to FIG. 2. The microcomputer 41 and the control circuit work to control the pump cell voltage Vp to be applied across the electrodes 32 and 33 of the pump cell 31, the monitor cell voltage Vm to be applied across the electrodes 36 and 38 of the monitor cell 34, and the sensor cell voltage Vs to be applied across the electrodes 37 and 38 of the sensor cell 35 in the manner, as described above. The microcomputer 41 samples the pump cell current Ip the monitor cell current Im, and the sensor cell current Is to determine the concentration of NOx contained in the exhaust gas.

Figure 2:
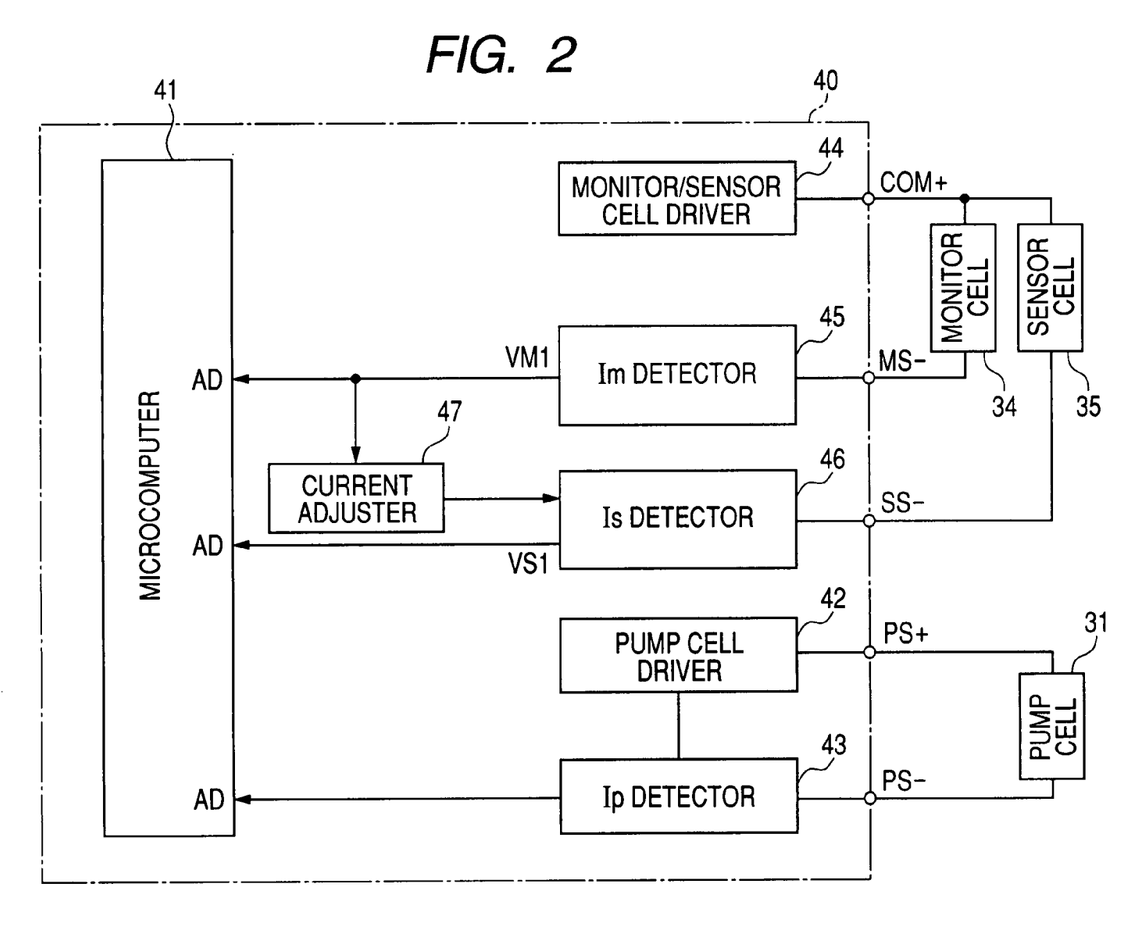
FIG. 2 is a circuit block diagram which shows a NOx sensor circuit installed in the gas sensor control system of FIG. 1.

FIG. 2 is a block diagram which shows an internal structure of the NOx sensor circuit 40. FIG. 2 omits a heater driver which is installed in the NOx sensor circuit 40 to control the operation of the heater 23 for the sake of simplicity of illustration.

The NOx sensor circuit 40 is equipped with a positive terminal PS+ and a negative terminal PS− connected to the electrodes 32 and 33 of the pump cell 31, respectively, a common terminal COM+ connected to the common electrode 38 of the monitor cell 34 and the sensor cell 35, and negative terminals MS− and SS− connected to the electrodes 36 and 37 of the monitor cell 34 and the sensor cell 35.

The NOx sensor circuit 40 also includes a pump cell driver 42, an Ip detector 43, a monitor/sensor cell driver 44, an Im detector 45, an Is detector 46, and a current adjuster 47. The pump cell driver 42 is connected to the positive terminal PS+ to apply the voltage to the pump cell 31. The Ip detector 43 is connected to the negative terminal PS− to measure the pump cell current Ip that is an electric current, as produced by the pump cell 31. The pump cell driver 42 works to control the voltage to be applied to the pump cell 31 as a function of the pump cell current Ip, as sampled by the Ip detector 43. The Ip detector 43 monitors the pump cell current Ip and input it to the microcomputer 41.

The sensor driver 44 is connected to the common positive terminal COM+ to apply the voltage to the monitor cell 34 and the sensor cell 35. The Im detector 45 is connected to the negative terminal MS to sample the monitor cell current Im that is an electric current, as produced by the monitor cell 34. The Is detector 46 is connected to the negative terminal SS− to sample the sensor cell current Is that is an electric current, as produced by the sensor cell 35. The Im detector 45 and the Is detector 46 are connected to the microcomputer 41 and output the monitor cell current Im and the sensor cell current Is to the microcomputer 41 as current-measured values VM1 and VS1.

The current-measured value VM1, as outputted from the Im detector 45, is also inputted to the current adjuster 47. An output of the current adjuster 47 is inputted to the Is detector 46. The current adjuster 47 works to produce an adjustment current as a function of the current-measured value VM1 outputted from the Is detector 45 and create a flow of the adjustment current in a direction in which it is discharged from the Is detector 46, thereby causing the Is detector 46 to produce the sensor cell current Is minus the adjustment current and output it to the microcomputer 41 as the current-measured value VS1.

Specifically, the current adjuster 47 produces the adjustment current which is identical in ampere with an instantaneous value of the monitor cell current Im. The Is detector 46, thus, subtracts the instantaneous value of the monitor cell current Im from the sensor cell current Is and outputs it (=Is−Im) to the microcomputer 41.

The structure of the above components of the NOx sensor circuit 40 will be described below with reference to FIGS. 3 and 4. The pump cell driver 42 and the Ip detector 43 are substantially identical with known typical ones, and explanation thereof in detail will be omitted here.

Figure 3:
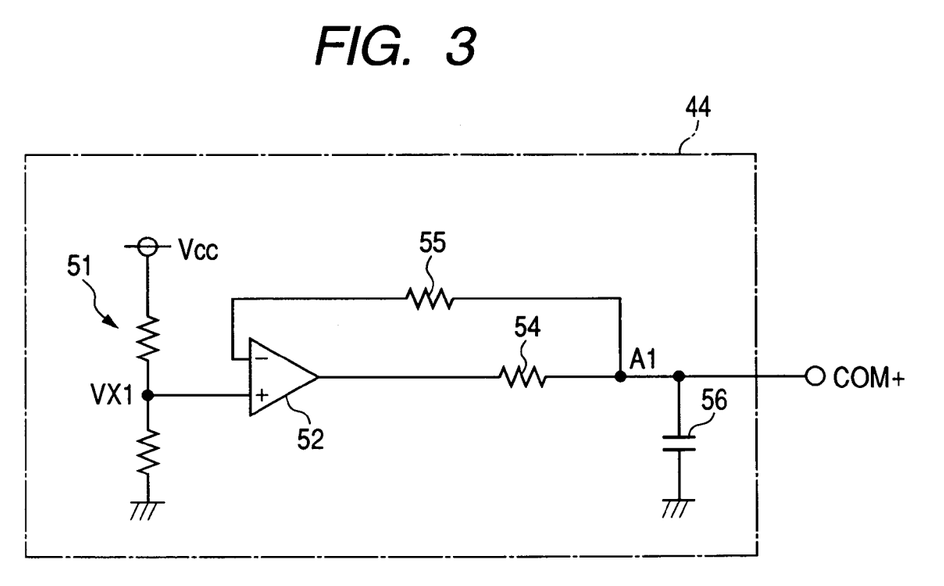
FIG. 3 is a circuit block diagram which shows a monitor/sensor cell driver installed in the NOx sensor circuit of FIG. 2.

FIG. 3 illustrates a circuit structure of the monitor/sensor cell driver 44. The monitor/sensor cell driver 44 includes a voltage divider 51, an operational amplifier 52, protective resistors 54 and 55, and a capacitor 56. The voltage divider 51 is made up of two resistors connected to a constant voltage source Vcc and works to make a fraction of an output of the constant voltage source Vcc and input it as voltage VX1 to a (+) input of the operational amplifier 52. The output of the operational amplifier 52 is connected to the common terminal COM+ through the protective resistor 54. A negative feedback terminal of the operational amplifier 52 is connected to the protective resistor 55. The capacitor 56 is connected to the common terminal COM+ for minimizing the electrostatic discharge (ESD).

Figure 4:
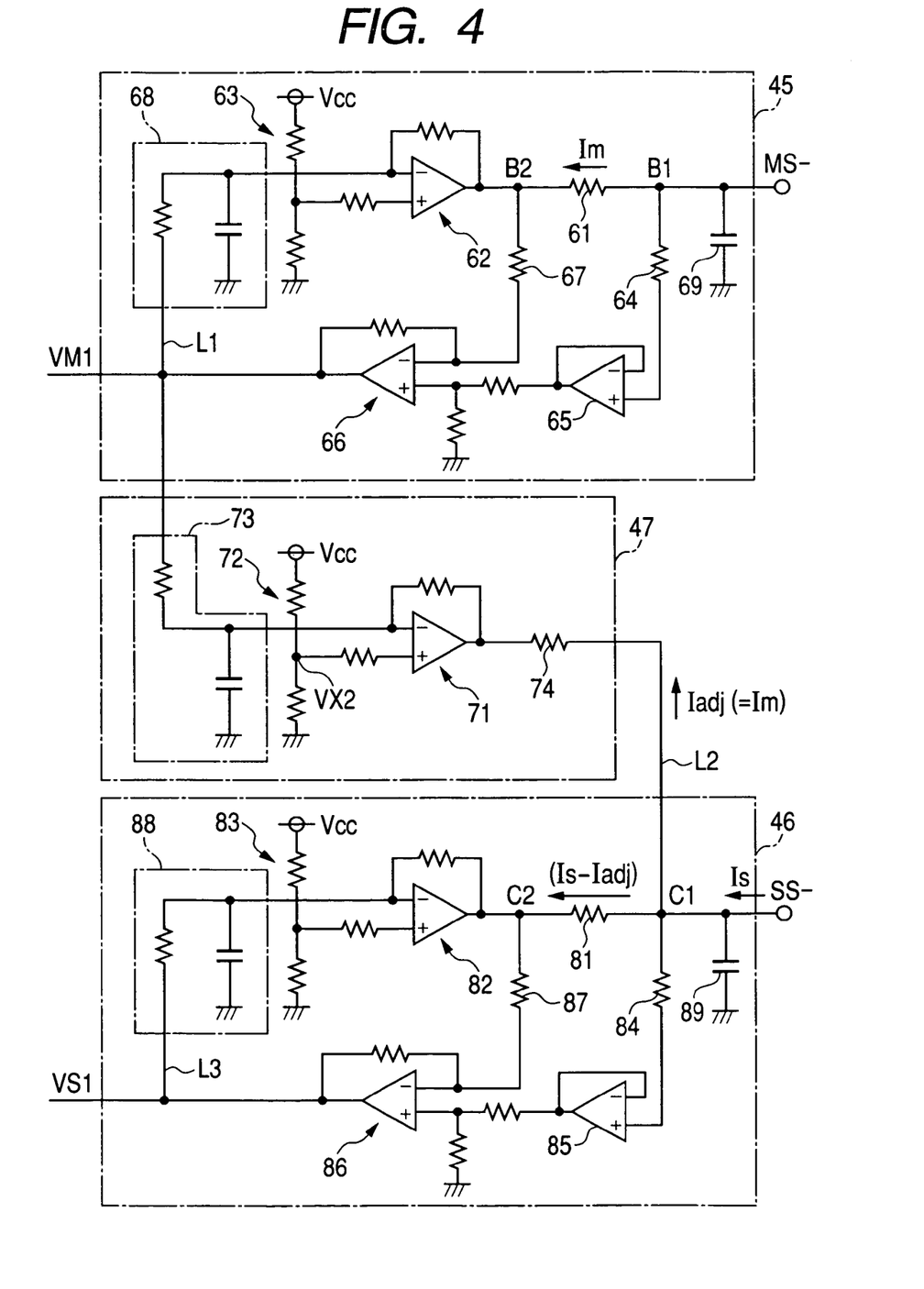
FIG. 4 is a circuit block diagram which shows an Im detector, a current adjuster, and an Is detector which are installed in the NOx sensor circuit of FIG. 2.
Figure 5A:
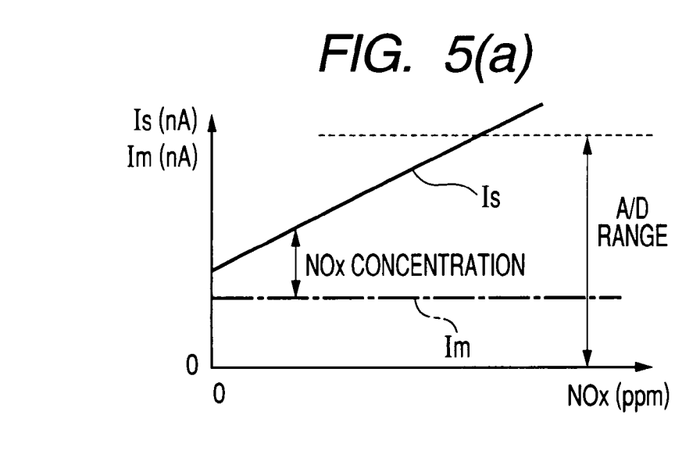
FIG. 5(a) is a view which represents the relation of the concentration of NOx in exhaust gas to a monitor cell current Im and a sensor cell current Is.
Figure 5B:
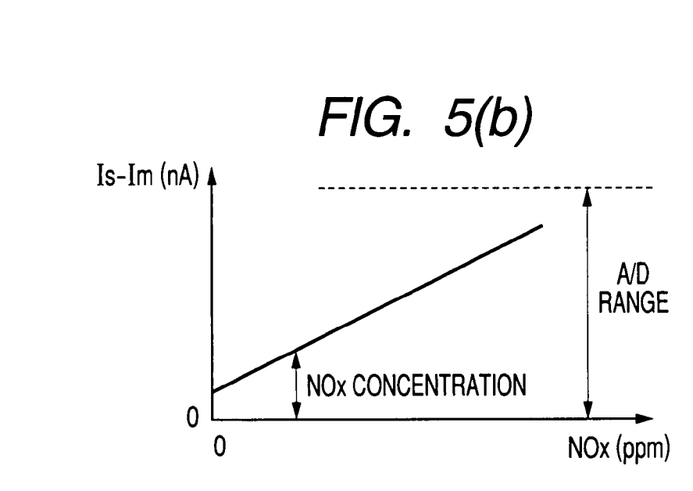
FIG. 5(b) is a view which represents the relation of the concentration of NOx to a sensor cell current Is minus a monitor cell current Im.
Figure 5C:
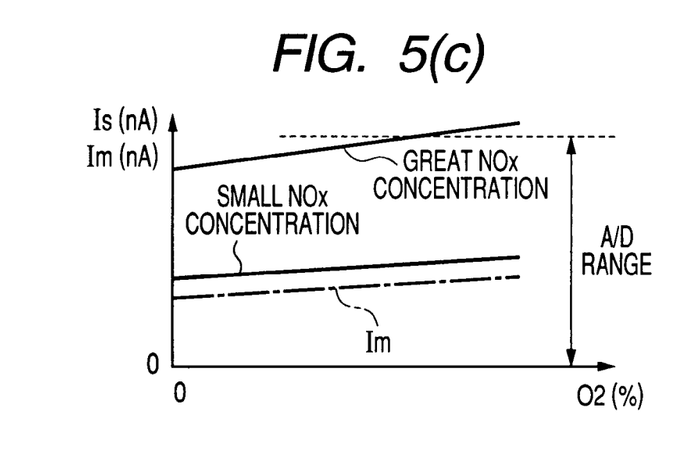
FIG. 5(c) is a view which represents the relation of the concentration of oxygen remaining in a second chamber in a sensing device to a sensor cell current Is and a monitor cell current Im.
Figure 5D:
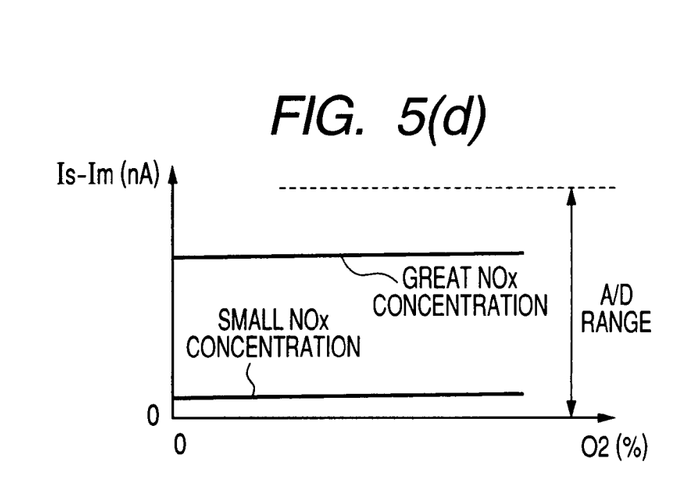
FIG. 5(d) is a view which represents the relation of the concentration of oxygen remaining in a second chamber of a sensing device to a sensor cell current Is minus a monitor cell current Im.

FIG. 4 illustrates circuit structures of the Im detector 45, the Is detector 46, and the current adjuster 47.

The Im detector 45 includes a current-measuring resistor 61, a differential amplifier 62, a voltage divider 63, a protective resistor 64, a voltage follower 65, a differential amplifier 66, a protective resistor 67, a low-pass filter 68, and a capacitor 69.

The current-measuring resistor 61 and the differential amplifier 62 are connected in series to the negative terminal MS− for the monitor cell 34. Specifically, the current-measuring resistor 61 is connected to an output of an operational amplifier which constitutes the differential amplifier 62 and disposed outside a negative feedback terminal of the differential amplifier 62. The voltage divider 63 is made up of two resistors and works to provide a fraction of an output of the constant voltage source Vcc to a (+) input terminal (i.e., a non-inverting input terminal) of the differential amplifier 62. A feedback input path L1 is joined to a (−) input terminal (i.e., an inverting input terminal) of the differential amplifier 62. The current-measuring resistor 61 and the differential amplifier 62 function as a current-to-voltage converter.

The voltage follower 65 is connected to a junction B1 (i.e., a sensor-side end of the current-measuring resistor 61) leading to the negative terminal MS−. The voltage follower 65 is connected at an output terminal thereof to a (+) input terminal of the differential amplifier 66. The differential amplifier 66 is connected at a (−) input terminal thereof through the protective resistor 67 to a junction B2 leading to one of the ends of the current-measuring resistor 61 which is farther away from the sensing device 10. When the monitor cell current Im flows through the current-measuring resistor 61, it will cause a potential difference to be developed between the junctions B1 and B2 (i.e., the ends of the current-measuring resistor 61) as a function of the monitor cell current Im. The differential amplifier 66 amplifies the potential difference at a given amplification factor and outputs it as the current-measured value VM1.

The current-measured value VM1, as outputted from the differential amplifier 66, is inputted to the (−) input terminal of the differential amplifier 62 through the feedback input path L1. The low-pass filter 68 is disposed in the feedback input terminal L1. The low-pass filter 68 is typically made up of a resistor and a capacitor.

The capacitor 69 is connected to the junction B1 for minimizing the electrostatic discharge (ESD). Specifically, the capacitor 69 is connected at one end to the current-measuring resistor 61 and at the other end to ground.

The current adjuster 47 is connected to an output terminal of the Im detector 45 (i.e., the output terminal of the differential amplifier 66). The current adjuster 47 includes a differential amplifier 71, a voltage divider 72, a low-pass filter 73, and a resistor 74. The differential amplifier 71 is connected at a (−) input terminal thereof to the output VM1 of the Im detector 45 and at a (+) input terminal thereof to a reference voltage VX2. Specifically, the differential amplifier 71 receives at the (−) input terminal the output VM1 from the Im detector 4 through the low-pass filter 73 made up of a resistor and a capacitor and connects at the (+) input terminal with the voltage divider 72. The voltage divider 72 is made up of two resistors and works to provide a fraction of the constant voltage Vcc to the (+) input terminal of the differential amplifier 71 as the reference voltage VX2.

A current path L2 extends from an output terminal of the differentia amplifier 71. The resistor 74 is disposed in the current path L2. The current path L2 is joined to a sensor-side terminal of a current-measuring resistor 81 of the Is detector 46 and serves as a branch path.

The current adjuster 47 is designed to determine the adjustment current Iadj based on the output VM1 of the Im detector 45 and establish a flow of the adjustment current Iadj in the current path L2 in a direction in which it is drawn from the Is detector 46. The adjustment current Iadj changes with a change in the output VM1 of the Im detector 45. Specifically, when the concentration of oxygen remaining in the second chamber 16 of the sensing device 10 increases, it will result in an increase in the output VM1 of the Im detector 45 (i.e., an increase in monitor cell current Im), so that the output of the differential amplifier 71 drops. This causes the adjustment current Iadj to increase. Conversely, when the concentration of oxygen remaining in the second chamber 16 of the sensing device 10 decreases, it will result in a decrease in the output VM1 of the Im detector 45 (i.e., a decrease in monitor cell current Im), so that the output of the differential amplifier 71 rises. This causes the adjustment current Iadj to decrease. The current adjuster 47 is designed to produce the adjustment current Iadj identical in level with the monitor cell current Im.

The structure of the Is detector 46 will be described below. which The Is detector 46 is substantially identical in structure with the Im detector 45.

The Is detector 46 includes a current-measuring resistor 81, a differential amplifier 82, a voltage divider 83, a protective resistor 84, a voltage follower 85, a differential amplifier 86, a protective resistor 87, a low-pass filter 88, and a capacitor 89.

The current-measuring resistor 81 and the differential amplifier 82 are connected in series to the negative terminal SS− for the sensor cell 35. Specifically, the current-measuring resistor 81 is connected to an output of an operational amplifier which constitutes the differential amplifier 82 and disposed outside a negative feedback terminal of the differential amplifier 82. The voltage divider 83 is made up of two resistors and works to provide a fraction of an output of the constant voltage source Vcc to a (+) input terminal of the differential amplifier 82. A feedback input path L3 is joined to a (−) input terminal of the differential amplifier 82. The current-measuring resistor 81 and the differential amplifier 82 function as a current-to-voltage converter.

The current path L2 extends from the current adjuster 47 to a junction C1 (i.e., a sensor-side end of the current-measuring resistor 81) leading to the negative terminal SS−. When the sensor cell current Is flows through the sensor cell-side negative terminal SS−, it is divided into a first current component (Is−adj) flowing through the current-measuring resistor 81 and a second current component (Iadj) flowing through the current path L2. In other words, the sensor cell current Is minus the adjustment current Iadj (=the monitor cell current Im) flows through the current-measuring resistor 81.

The voltage follower 85 is connected to the junction C1 through the protective resistor 84. The voltage follower 85 is joined at an output terminal thereof to a (+) input terminal of the differential amplifier 86. The differential amplifier 86 is connected at a (−) input terminal thereof through the protective resistor 87 to a junction C2 leading to one of the ends of the current-measuring resistor 81 which is farther away from the sensing device 10. When the current (Is−Iadj) flows through the current-measuring resistor 81, it will cause a potential difference to be developed between the junctions C1 and C2 (i.e., the ends of the current-measuring resistor 81) as a function of the current (Is−Iadj). The differential amplifier 86 amplifies the potential difference at a given amplification factor and outputs it as the current-measured value VS1.

The current-measured value VS1, as outputted from the differential amplifier 86, is inputted to the (−) input terminal of the differential amplifier 82 through the feedback input path L3. The low-pass filter 88 is disposed in the feedback input terminal L3. The low-pass filter 88 is typically made up of a resistor and a capacitor.

The capacitor 89 is connected to the junction C1 for minimizing the electrostatic discharge (ESD). Specifically, the capacitor 89 is connected at one end to the current-measuring resistor 81 and at the other end to ground.

The microcomputer 41, as illustrated in FIG. 2, receives the current-measured value VS1 outputted from the Is detector 46 through an A/D converter and uses it to calculate the concentration of NOx contained in the exhaust gas of the engine.

As described above, the current flowing through the current-measuring resistor 81 of the Is detector 46 is the sensor cell current Is minus the adjustment current Iadj (Is−Iadj=Is−Im). Specifically, the Is detector 46 measures the current smaller than the sensor cell current Is, thereby permitting the resolution in current-to-voltage conversion to be increased. For example, the resistance value of the current-measuring resistor 81 and/or the signal amplification factor may be increased.

The current-measured value VS1 to be inputted to the microcomputer 41 is a voltage signal corresponding to the sensor cell current Is minus the adjustment current Iadj (Is−Iadj=Is−Im), thereby permitting the range of the A/D converted signal inputted to the microcomputer 41 to be decreased to increase the resolution of the A/D conversion.

The relations between the concentration of NOx and the outputs (i.e., the monitor cell current Im and the sensor cell current Is) from the sensing device 10 and between the concentration of oxygen ($O_2$) remaining in the second chamber 16 and the outputs from the sensing device 10 will be described below with reference to FIGS. 5(*a*) to 5(*d*).

FIG. 5(*a*) represents the relation of the concentration of NOx in the exhaust gas to the monitor cell current Im and the sensor cell current Is. FIG. 5(*a*) represents the relation of the concentration of NOx to the sensor cell current Is minus the monitor cell current Im. FIG. 5(*c*) represents the relation of the concentration of oxygen remaining in the second chamber 16 to the sensor cell current Is and the monitor cell current Im. FIG. 5(*d*) represents the relation of the concentration of oxygen remaining in the second chamber 16 to the sensor cell current Is minus the monitor cell current Im. In FIGS. 5(*a*) and 5(*c*), a solid line indicates the sensor cell current Is. A dashed line indicates the monitor cell current Im.

FIG. 5(*a*) shows that the sensor cell current Is contains the monitor cell current Im and that an increase in concentration of NOx may cause the sensor cell current Is to be out of an analog-to-digital (A/D) conversion range. FIG. 5(*b*) shows that even when the concentration of NOx increases, the sensor cell current Is minus the monitor cell current Im (Is−Im) that is to be inputted to the microcomputer 41 may be A/D converted within the A/D conversation range. FIG. 5(*c*) shows that an increase in concentration of oxygen remaining in the second chamber 16 may cause the sensor cell current Is to be out of the A/D conversion range when the concentration of NOx exceeds a certain value. FIG. 5(*d*) shows that the sensor cell current Is minus the monitor cell current Im (Is−Im) that is to be inputted to the microcomputer 41 to be A/D converted within the A/D conversation range.

As apparent from the above discussion, the NOx sensor circuit 40 has the following beneficial advantages.

The NOx sensor circuit 40 is, as described above, designed to determine the adjustment current Iadj based on the output VM1 of the Im detector 45 and establish a flow of the adjustment current Iadj in the current path L2 which leads to one of the ends of the resistor 81 of the Is detector 46 closer to the sensing device 10, so that the current that is the sensor cell current Is minus the adjustment current Iadj may flow through the current-measuring resistor 81. This causes the Is detector 46 to sample the current smaller than the sensor cell current Is by the adjustment current Iadj, thereby permitting the resolution in current-to-voltage conversion to be increased and also the resolution of the A/D conversion in the microcomputer 41 to be increased.

The current adjuster 47 is designed to select the adjustment current Iadj as a function of the output VM1 of the Im detector 45 and establish a flow of the adjustment current Iadj in a direction in which it is drawn from the Is detector 46. This causes the adjustment current Iadj to be changed with a change in the output VM1 of the Im detector 45. The current that is the sensor cell current Is minus the instantaneous value of the monitor cell current Im is, therefore, processed in the Is detector 46.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

Figure 6:
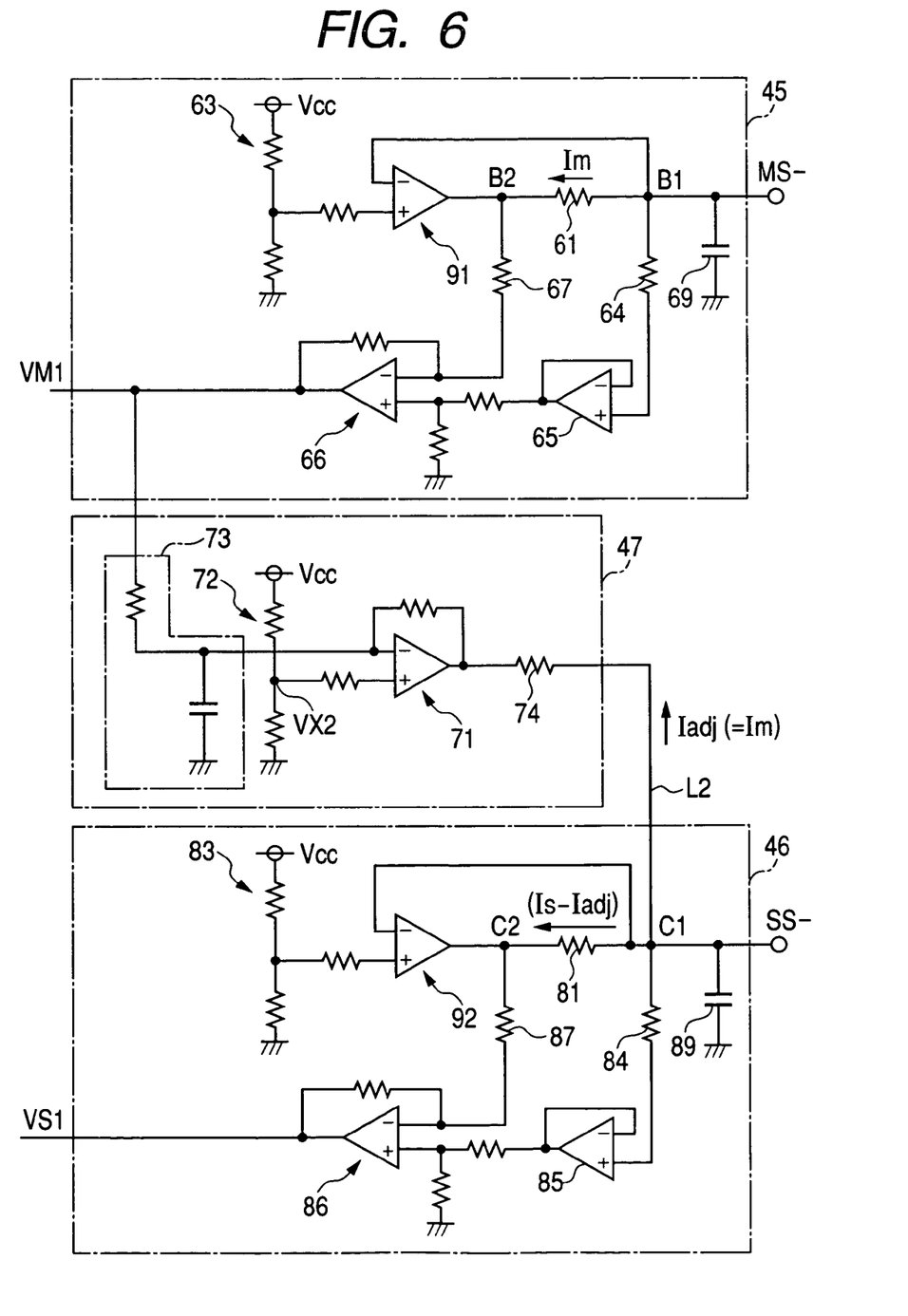
FIG. 6 is a circuit block diagram which shows modifications of the Im detector, the current adjuster, and the Is detector, as illustrated in FIG. 4.

The Im detector 45 and the Is detector 46 may be designed to have the structures, as illustrated in FIG. 6. The same reference numbers, as employed in FIG. 4, refer to the same parts, and explanation thereof in detail will be omitted here.

Specifically, the Im detector 45 is different from the one in FIG. 4 in that an inverting amplifier 91 is used instead of the differential amplifier 62. Similarly, the Is detector 46 is different from the one in FIG. 4 in that an inverting amplifier 92 is used instead of the differential amplifier 82. The current that is the sensor cell current Is minus the adjustment current Iadj flows through the current-measuring resistor 81 in the Is detector 46, thereby permitting the resolution in current-to-voltage conversion to be increased.

The monitor cell 34 and the sensor cell 35 may be different in sensitivity of electric current to the concentration of oxygen remaining in the second chamber 16 due to a difference in material or area or size of the electrodes 36 and 37. In this case, the current adjuster 47 is preferably designed to compensate for a difference in the sensitivity to the concentration of oxygen between the monitor cell 34 and the sensor cell 35. This may be achieved by adjusting the amplification factor of the differential amplifier 71 of the current adjuster 47, thereby resulting in improvement of accuracy in measuring the concentration of NOx.

In the above embodiment, the adjustment current Iadj is set identical with the monitor cell current Im, but however, they may be different from each other as long as the adjustment current Iadj is a function of the monitor cell current Im. For example, the adjustment current Iadj may be determined according to an equation of Iadj=Im×α where α is a predetermined constant.

The monitor cell 34 and the sensor cell 35 share the common terminal COM+ used as the positive terminal, but however, the positive terminal of one of the monitor cell 34 and the sensor cell 35 may be shared with the negative terminal of the other. In this case, the Im detector 45 and the Is detector 46 are connected to the terminals of the monitor cell 34 and the sensor cell 35 which are not shared with each other.

The gas sensor control system may alternatively be designed to measure HC, CO, or $NH_3$ contained in exhaust emissions from the engine. In this case, the pump cell 31 works to pump out oxygen molecules contained in the exhaust emissions. The sensor cell 35 works to decompose or ionize HC, CO, or $NH_3$ contained in the exhaust emissions from which oxygen molecules have been discharged and output a signal indicative of the concentration of HC, CO, or $NH_3$.

The gas sensor control system may be used with a gas sensor installed in an intake pipe of a diesel engine or a gasoline engine or a gas sensor installed in an exhaust pipe of the gasoline engine. The gas sensor control system may also be used with a gas sensor designed to measure the concentration of gas which is other than the exhaust gas of the engine or emitted from other than automotive engines.

What is claimed is:

1. A gas sensor control system for controlling an operation of a gas sensor equipped with a sensing device including a first cell, a second cell, and a third cell which are each made of a solid electrolyte and a gas chamber formed therein, the first cell working to control an amount of oxygen contained in a gas admitted into the gas chamber to keep a concentration of oxygen in the gas at a given controlled level, the second cell working to produce an electric current as a function of a concentration of oxygen contained in the gas in which the amount of oxygen has been controlled by the first cell, the third cell working to produce an electric current as a function of a concentration of a preselected component of the gas in which the amount of oxygen has been controlled by the first cell, comprising:

a second cell circuit including a current-to-voltage converter which is connected to the second cell to sample and convert the electric current, as produced by the second cell, into a voltage and outputs the voltage as a second cell current-measured value;

a third cell circuit including a current-to-voltage converter which is connected to the third cell;

a current adjuster working to produce an adjustment current that is an electric current determined as a function of the second cell current-measured value, as outputted from said second cell circuit; and a branch circuit path which is connected to a junction between the current-to-voltage converter of the third cell circuit and the third cell and through which the adjustment current flows to input the electric current, as produced by the third cell, minus the adjustment current into the current-to-voltage converter of the third cell circuit, so that the current-to-voltage converter converts the electric current minus the adjustment current into a voltage and outputs the voltage as a third cell current-measured value representing the concentration of the preselected component of the gas, wherein subtraction of the adjustment current from the electric current, as produced by the third cell, is performed, and then a difference between the adjustment current and the electric current is inputted to the current-to-voltage converter of the third cell circuit, and wherein:

said current adjuster is connected to an output terminal of the second cell circuit and is configured to determine the adjustment current based on the second cell current-measured value, as outputted from said second cell circuit and establish a flow of the adjustment current through said branch circuit path in a direction in which the adjustment current is drawn from the third cell circuit, said current adjuster produces the adjustment current which is identical with the electric current, as produced by the second cell, said current adjuster is designed to regulate a difference between a sensitivity of the second cell to produce the electric current in response to the concentration of oxygen and that of the third cell to produce the electric current in response to the concentration of oxygen; and the gas sensor control system further comprises an analog-to-digital converter into which the third cell current-measured value, as outputted from said third cell circuit, is inputted and converts the third cell current-measured value into a digital signal as indicating the concentration of the preselected component of the gas.

2. A gas sensor control system as set forth in claim 1, wherein said current adjuster is equipped with a differential amplifier which has one of two input terminals into which the second cell current-measured value is inputted and the other input terminal to which a reference voltage is inputted and also has an output terminal connected to said branch circuit path.

* * * * *